US00PP23416P2

(12) United States Plant Patent
Brennan

(10) Patent No.: US PP23,416 P2
(45) Date of Patent: Feb. 26, 2013

(54) BLACK CURRANT PLANT NAMED 'BEN COMO'

(50) Latin Name: *Ribes nigrum*
Varietal Denomination: Ben Como

(75) Inventor: Rex M. Brennan, Fife (GB)

(73) Assignee: James Hutton Institute, Invergowrie (GB)

( * ) Notice: Subject to any disclaimer, the term of this patent is extended or adjusted under 35 U.S.C. 154(b) by 0 days.

(21) Appl. No.: 13/317,788

(22) Filed: Oct. 27, 2011

(51) Int. Cl.
*A01H 5/00* (2006.01)
(52) U.S. Cl. ..... Plt./156
(58) Field of Classification Search ..... Plt./156
See application file for complete search history.

*Primary Examiner* — Annette Para
(74) *Attorney, Agent, or Firm* — Penny J. Aguirre

(57) ABSTRACT

A new cultivar of *Ribes nigrum*, 'Ben Como', characterized by its consistent high yields of fruit, its upright and compact growth habit, its high degree of fruit set, its resistance to white pine blister rust and its suitability for machine harvesting, and in producing a larger plant, smaller berry, and fruit that ripens later than 'Ben Chaska'.

2 Drawing Sheets

Botanical classification: *Ribes nigrum.*
Cultivar designation: 'Ben Como'.

CROSS REFERENCE TO A RELATED APPLICATION

This application is co-pending with a U.S. Plant Patent Application filed for a plant derived from the same breeding program that is entitled *Ribes* Plant Named 'Ben Chaska' (U.S. Plant patent application Ser. No. 13/317,787).

BACKGROUND OF THE INVENTION

The present invention relates to a new and distinct cultivar of *Ribes nigrum* named 'Ben Como' and is hereinafter referred to by the cultivar name 'Ben Como'. 'Ben Como' represents a new cultivar of black currant grown for fruit production.

The new cultivar was derived from a controlled breeding program by the Inventor in Invergowrie, Scotland. The Inventor made a cross in 1984 between an unnamed proprietary plant in the Inventor's breeding program, reference no. SCRI P10/9/20, as the female parent and reference no. Ri-74020-16 as the male parent. The Inventor selected 'Ben Como', reference no. SCRI D16/8/14 in 1986 as a single unique plant amongst the seedlings that resulted from the above cross.

Asexual reproduction of the new cultivar was first accomplished under direction of the Inventor by hardwood cuttings in Dundee, Scotland in 1990. Asexual reproduction of the new cultivar has shown that the unique features are stable and reproduced true to type in successive generations.

SUMMARY OF THE INVENTION

The following traits have been repeatedly observed and represent the characteristics of the new cultivar. These attributes in combination distinguish 'Ben Como' as a new and unique cultivar of *Ribes nigrum.*

1. 'Ben Como' exhibits consistently high yields of fruit.
2. 'Ben Como' exhibits an upright and compact growth habit.
3. 'Ben Como' exhibits a high degree of fruit set.

4. 'Ben Como' exhibits resistance to white pine blister rust (*Cronartium ribicola*).
5. 'Ben Como' is readily harvested by machines.
6. 'Ben Como' produces a larger plant, smaller berry, and fruit that ripens later than 'Ben Chaska'.

'Ben Como' can be readily compared to its parent plants. SCRI P10/9/20, the female parent, differs from 'Ben Como' in lacking resistance to white pine blister rust, in being less cold hardy, in having a less compact plant habit, and in exhibiting less fruit set. Ri-74020-16, the male parent, differs from 'Ben Como' in having a poorer growth rate and less vigor, in having less consistent and lower fruit yields, and in lacking suitability for machine harvest. 'Ben Como' can be most closely compared to the cultivars 'Titania' (U.S. Plant Pat. No. 11,439) and 'Ben Lomond' (not patented). 'Titania' is similar to 'Ben Como' in exhibiting resistance to white pine blister rust, but differs from 'Ben Como' in having less consistent and lower crop levels, in having a less compact and less manageable plant habit, and in flowering later in the season. 'Ben Lomond' is similar to 'Ben Como' in having a high fruit yield, but differs from 'Ben Como' in lacking resistance to white pine blister rust and powdery mildew (*Sphaerotheca mors-uvae*), in having a less compact and less upright plant habit, and in having poorer fruit quality in terms of juice color and flavor. 'Ben Como' can also be compared to the cultivar 'Ben Chaska' (U.S. Plant Patent pending)*, a cultivar from the same breeding program. 'Ben Como' is similar to 'Ben Chaska' in having a consistently high yields, in having a compact and upright growth habit, in degree of fruit set, and in being resistant to white pine blister rust. 'Ben Chaska' differs from 'Ben Como' in flowering slightly earlier in the season, in having a lower vigor, smaller plant size, and larger fruit than 'Ben Como'.

BRIEF DESCRIPTION OF THE DRAWING

The accompanying colored photographs illustrate the overall appearance and distinct characteristics of the new *Ribes* cultivar. The photographs were taken of five year-old plants of the new cultivar as grown outdoors in a field in Becker, Minn.

The photograph in FIG. 1 provides a view of the habit of 'Ben Como' (plants in the front of the row) in comparison to the plant habit of 'Titania' (plants in the back of the row).

Figure 1:
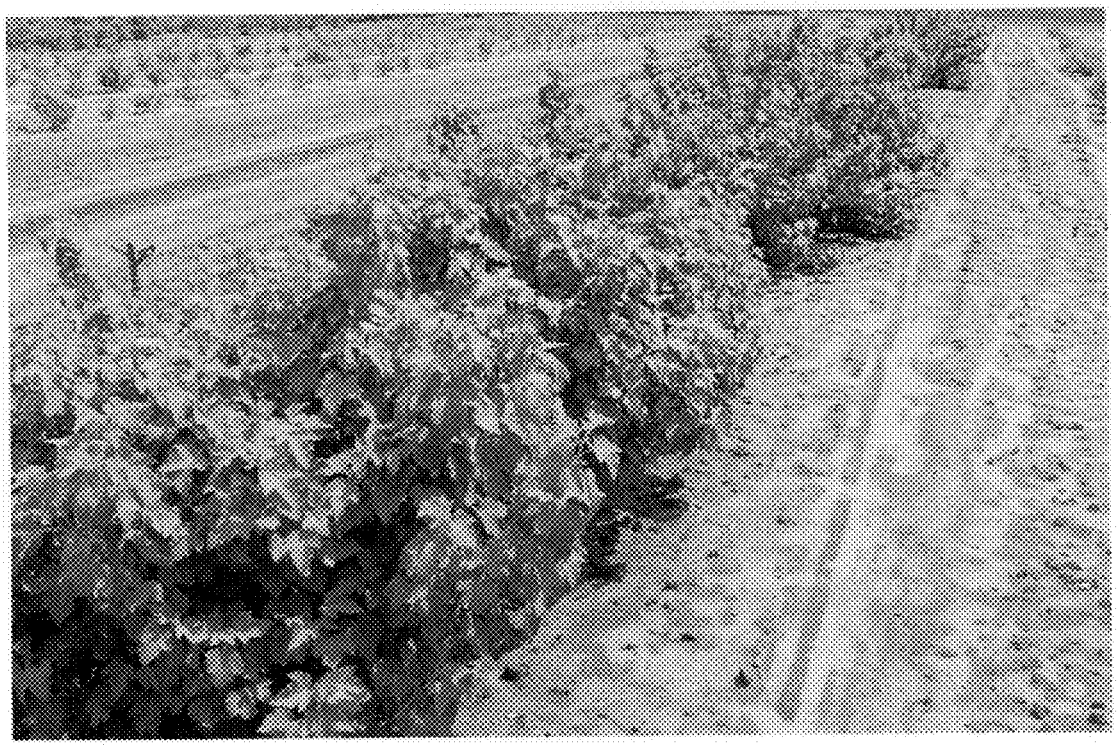
Figure 2:
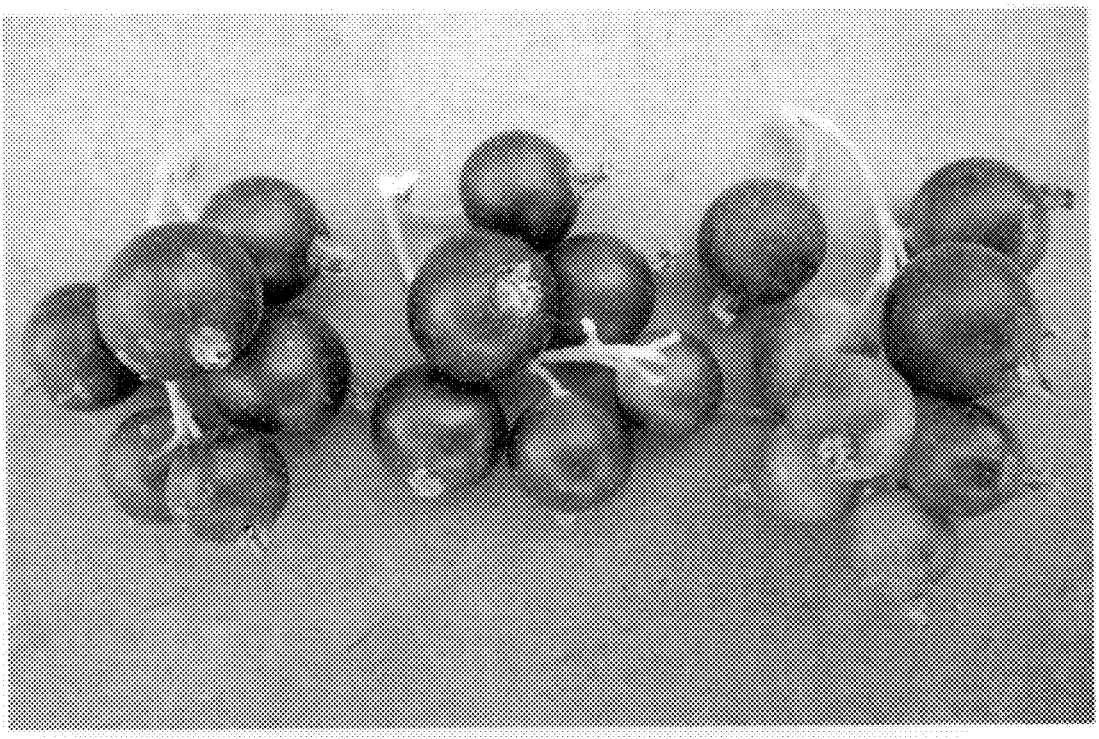

The photograph in FIG. 2 provides a close-up view of the fruit of 'Ben Como'.

Figure 3:
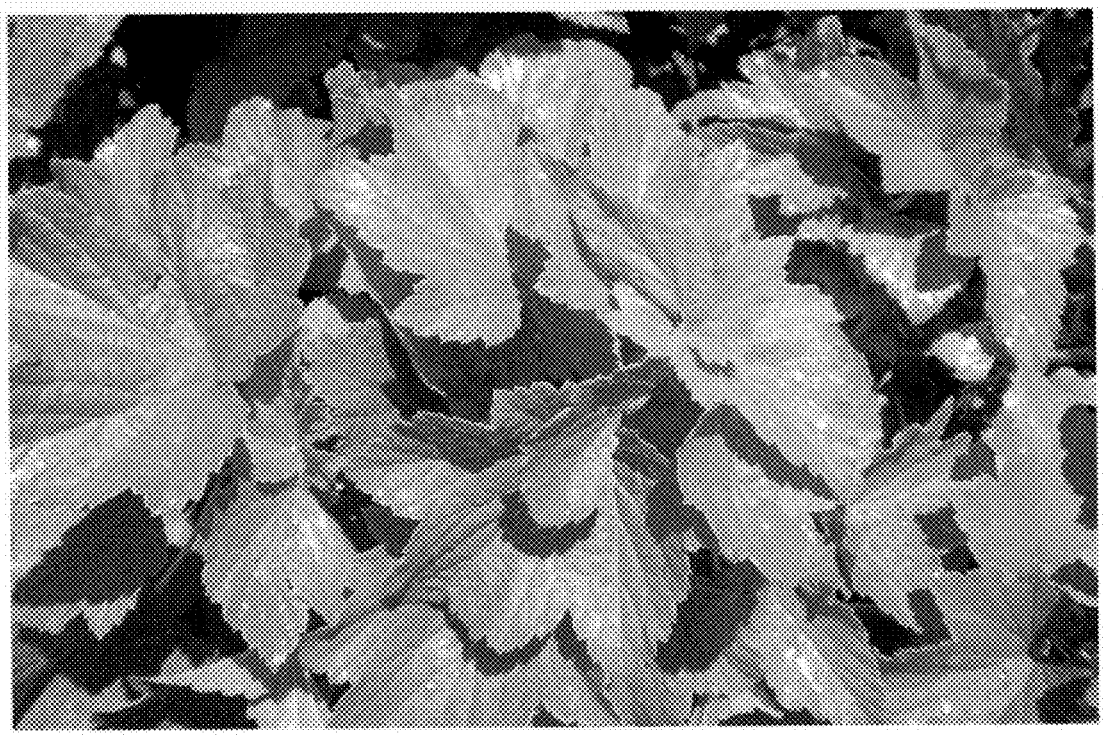

The photograph in FIG. 3 provides a close-up view of the foliage 'Ben Como'. The colors in the photographs are as close as possible with digital photography techniques available, the color values cited in the detailed botanical description accurately describe the colors of the new cultivar of *Ribes*.

DETAILED BOTANICAL DESCRIPTION OF THE PLANT

The following is a detailed description of plants 10 years in age as grown outdoors in a trial field in Becker, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Perennial shrub.

*Plant habit*.—Upright and compact.

*Height and spread*.—Reaches about an average of 1.4 m in height and 2.2 m in width.

*Cold hardiness*.—At least in U.S.D.A. Zone 4.

*Diseases and pests*.—Observed to be resistant to white pine blister rust (*Cronartium ribicola*) with improved powdery mildew (*Sphaerotheca mors-uvae*) resistance.

*Culture*.—Readily machine harvested.

*Propagation*.—Hardwood and greenwood (softwood) cuttings.

*Growth rate*.—Moderate to vigorous.

Stem description:

*Stem*.—Mature stem 200C in color; new growth, N200D in color, surface is glabrous on new growth with smooth bark when mature, main branches up to 1.4 m in length and an average of 7 mm in width.

*Leaf bud shape*.—Obclavate, bracts imbricate.

*Leaf bud size*.—Average 8 mm in length, 3 mm in width.

*Number of leaf buds*.—On 20 cm long stem average of 20 buds, ranging from 6 to 30 buds, per stem.

*Bracts*.—Deltoid in shape, apex retuse to subacute, base truncate, average 5 mm in width, 5 mm in length, turning dry and papery, margin entire and fimbriate, inner surface 52C in color to 56A towards base, turning 164A when dry, outer surface 51A in color to 51D towards base turning 164A when dry, glabrous on upper surface, glandular on lower surface; glands <1 mm in diameter, round in shape, 14B in color.

Foliage description:

*Leaf shape*.—Ovate.

*Leaf division*.—Simple.

*Leaf base*.—Cordate to auriculate.

*Leaf apex*.—Subacute.

*Leaf venation*.—Pinnate, color on upper and lower surface 145B, slightly puberulent with fine minute hairs on lower surface.

*Leaf margins*.—3 to 5 lobed to palmatifid with margins serrate.

*Leaf attachment*.—Petiolate.

*Leaf arrangement*.—Alternate clusters of 5-7 leaves, cluster base sheathed by bracts averaging 6 mm in length and 4 mm in width, N199D to 166D in color.

*Leaf orientation*.—Upright to 20 degree from main stem.

*Leaf surface*.—Upper surface glabrous, lower surface glandular.

*Leaf color*.—Upper surface ranging from 139B to 141B; lower surface ranging from 138B and 137C.

*Leaf size*.—Average of 1.5 cm in length (ranging from 0.5 cm to 2.2 cm), an average of 2.8 cm in width (ranging from 1 cm to 4 cm in width).

*Leaf quantity*.—About 45 per 20 cm stem.

*Petioles*.—Round in shape, an average of 3.8 cm in length and 1 mm in width, 144A in color, surface minutely puberulent.

*Stipules*.—None observed.

Inflorescence description:

*Bloom season*.—April 25 to May 5 in Becker, Minn.

*Inflorescence*.—Drooping raceme, average 2.3 cm in length 1.5 cm in width, 15 racemes per stem 20 cm in length.

*Lastingness of inflorescence*.—5 to 12 days depending on weather conditions at time of bloom.

*Pedicels*.—Round 1 mm in width, 1 to 3 mm in length, 145B in color, surface has sparse hairs, minute bract at base of pedicel; <1 mm in length and width, same color as leaves.

*Peduncles*.—Round, an average of 2.2 cm in length and 2.5 mm in width, surface has sparse hairs, 145B in color.

*Flowers*.—Campanulate, 6 to 11 flowers per raceme.

*Flower buds*.—Globose in shape, 2 to 4 mm in length and width, 144B in color.

*Flower size*.—Average of 5 mm in length, 6 mm in width.

*Sepals*.—Five, strongly recurved, 2 mm in width, 6 mm in length fused at base, color 144A on upper and 144B on lower surface, rounded apex, margins entire, sparsely pubescent on upper surface and pubescent on lower surface.

*Petals*.—Five fused in hypanthium, 2 mm in length, 1 mm in width, 145D in color on upper and lower surface, glabrous on upper and lower surface.

*Androecium*.—Epipetalous, anthers are basifixed, 160B in color, 1 mm in length, 0.5 mm in width, filaments 2 mm in length, <0.5 mm in width, 144B in color.

*Gynoecium*.—1, style is 4 mm in length, 1 mm in width, 145B in color, ovary is inferior, 4 mm in length and 4 mm in width, globose in shape, 144D in color, bifid stigma is minute 144D to N137A in color.

Fruit description:

*Fruit number*.—30 to 70 fruits per branch 30 cm long.

*Fruit yield*.—2.7 kg per plant in Becker, Minn. on 5 year-old plants (compares to 2.2 kg for 'Titania' and 1.6 kg for 'Ben Chaska' in the same trial).

*Fruit set*.—High, 65 to 80%.

*Fruit size*.—1.1 cm in diameter and height.

*Fruit weight*.—Average of 114.05 g/100 berries.

*Fruit chemistry*.—Averages: Brix 14.4, specific gravity 1.0603, acidity 4.2065 g/L tartaric and 3.93 g/L citric, anthoncyanins 1.274 (430 nm), 3.0145 (515 nm), 0.529 (580 nm), ascorbic acid 71.1 ml/100 ml.

*Position of maximum diameter*.—Midway between proximal and distal ends.
*Fruit shape*.—Globose.
*Fruit symmetry*.—Symmetric.
*Persistence of calyx*.—Persistent at harvest, N199C in color, 3 mm in length.
*Surface*.—Glossy, smooth except for slightly protruding lenticels.
*Lenticels*.—50 to 65 per fruit, 200D in color.
*Waxiness of skin*.—Weak.
*Thickness of skin*.—Thin.
*Skin color*.—Immature 178A, maturing 186B, mature 202A.
*Color of flesh*.—Blend of 160B.
*Fruit maturity date*.—Early July.
*Seed*.—Ovate, 20 per fruit, 1.6 mm in length, 15 mm in width, 163A in color.
*Firmness* (*without skin*).—Soft.
*Texture of flesh*.—Pulpy, juicy.
*Cropping frequency*.—Annually.
*Flavor*.—Sweet, tart.

It is claimed:

1. A new and distinct cultivar of Black Currant plant named 'Ben Como' as herein illustrated and described.

* * * * *